(12) United States Patent
Daiss et al.

(10) Patent No.: US 8,722,914 B2
(45) Date of Patent: *May 13, 2014

(54) SILAOXACYCLES

(75) Inventors: Juergen Oliver Daiss, Munich (DE); Stefan Schmid, Munich (DE)

(73) Assignee: Wacker Chemie AG, Munich (DE)

( * ) Notice: Subject to any disclaimer, the term of this patent is extended or adjusted under 35 U.S.C. 154(b) by 46 days.

This patent is subject to a terminal disclaimer.

(21) Appl. No.: 13/636,544

(22) PCT Filed: Mar. 8, 2011

(86) PCT No.: PCT/EP2011/053487
§ 371 (c)(1),
(2), (4) Date: Sep. 21, 2012

(87) PCT Pub. No.: WO2011/117071
PCT Pub. Date: Sep. 29, 2011

(65) Prior Publication Data
US 2013/0018200 A1 Jan. 17, 2013

(30) Foreign Application Priority Data
Mar. 22, 2010 (DE) .......................... 10 2010 003 108

(51) Int. Cl.
*C07F 7/00* (2006.01)
(52) U.S. Cl.
USPC ........................................................ 556/443
(58) Field of Classification Search
USPC ........................................................ 556/443
See application file for complete search history.

(56) References Cited

U.S. PATENT DOCUMENTS

| | | | |
|---|---|---|---|
| 2,898,346 | A | 8/1959 | Eynon |
| 3,193,567 | A | 7/1965 | Rossmy |
| 5,371,262 | A | 12/1994 | Arkles |

FOREIGN PATENT DOCUMENTS

| | | |
|---|---|---|
| DE | 1251961 | 10/1967 |
| DE | 4407437 A1 | 9/1994 |
| EP | 0049155 A2 | 4/1982 |
| EP | 0073027 A2 | 3/1983 |
| EP | 0093806 A1 | 11/1983 |
| EP | 0106062 A2 | 4/1984 |
| EP | 0107211 A2 | 5/1984 |
| EP | 2120115 A2 | 11/2009 |
| EP | 2129121 A1 | 12/2009 |

OTHER PUBLICATIONS

John L. Speier et al.,Journal of Organic Chemistry 1960, Bd. 25, Dehydration of 1,3-Bis(hydroxyalkyl) tetramethyldisiloxanes, S. 1637-1640.
Walter Simmler et al, "Sila-dioxane, -dioxolane und -trioxane", Chemische Berichte 1966, Band 99, S. 1368-1383.
W. Simmler et al, "Direct Routes to the Isomeric Disilia -1.4-dioxanes", Organosilicon Chemistry, Scientific Communications, Prague, 1965, S. 120-124.
R, Tacke et al., "2.2.5.5-Tetraorganyl-1.4-dioxa-2.5-disilacycyclohexane", Zeitschrift fuer Naturforschung B, 1983, Band 38, S. 191-193.
Stefan Altmann et al., Monatshefte fuer Chemie 2003, Band 134, S. 1081-1092, "The Hydrolysis/Condensation Behaviour of Methacryloxyloxyalkylfunctional Alkoxysilanes: Structure-Reactivity Relations".
Chemical Lexicon ROEMPP Online (http://www.roempp.com/prod/roempp.php), Version 3.28, Article under "Periodensystem" issued Aug. 2006, pp. 1-7.

*Primary Examiner* — Johann R Richter
*Assistant Examiner* — Kofi Adzamli
(74) *Attorney, Agent, or Firm* — Brooks Kushman P.C.

(57) ABSTRACT

Siloxacycles are synthesized in high yield and purity by reaction of acyloxymethyl (alkoxy) silanes in the presence of a catalyst which is a metal from groups 3 to 15 of the periodic table, or a compound thereof.

9 Claims, No Drawings

SILAOXACYCLES

CROSS-REFERENCE TO RELATED APPLICATIONS

This application is the U.S. national phase of PCT Appln. No. PCT/EP2011/053487 filed Mar. 8, 2011 which claims priority to German application 10 2010 003 108.9 filed Mar. 22, 2010, the disclosures of which are incorporated in their entirety by reference herein.

BACKGROUND OF THE INVENTION

1. Field of the Invention

The present invention relates to a process for preparing silaoxacycles having structural units in which silicon and oxygen atoms are bonded to one another via a $CH_2$ group, and to novel silaoxacycles.

2. Description of the Related Art

Silaoxacycles in which silicon and oxygen atoms are bonded to one another via a $CH_2$ group are excellent reagents for the preparation of (hydroxymethyl)-polysiloxanes by termination of silicone oils according to the following reaction equation:

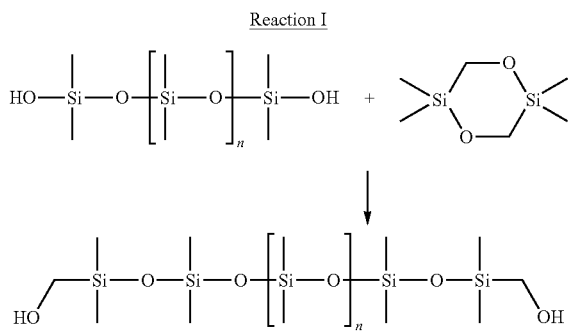

Reaction I

Since the silaoxacycle used as the terminating reagent, being a cyclic compound, has no end groups or the like which have to be eliminated in the reaction, the reaction I is a smooth addition reaction without any condensation products which would have to be removed thereafter. The thus produced carbinol oil terminated with Si—$CH_2$—OH groups is of excellent suitability for the preparation of "AA-BB" polymers, for example by reaction with diisocyanates, assuming that the termination is quantitative, since every Si—OH group which is not terminated with an Si—$CH_2$—OH group is converted in the course of subsequent preparation of AA-BB polymers by means of diisocyanates to an Si—O—C(O)—NH— group, the Si—O bond of which constitutes a hydrolysis-sensitive cleavage site. The greater the purity of the silaoxacycle used, the smoother the termination.

The specialist literature describes various methods for preparation of silaoxacycles in which silicon and oxygen atoms are bonded to one another via a $CH_2$ group.

For instance, the preparation of 2,2,5,5-tetramethyl-1,4-dioxa-2,5-disilacyclohexane by heating of 1,3-bis-(hydroxymethyl)-1,1,3,3-tetramethyldisiloxane over calcium oxide has been described in U.S. Pat. No. 2,898,346 and Journal of Organic Chemistry 1960, vol. 25, p. 1637-1640. However, this process gives the product only in a 40-60% yield, requires the use of calcium oxide in an amount of about one quarter of the reaction mass, and gives an impure product, recognisable by the broad boiling range of the product fraction and by the elemental analysis reported, which has distinct deviations from the theoretical values. The poor purity of the product thus prepared is confirmed by Chemische Berichte 1966, vol. 99, p. 1368-1383 (see footnote 10 therein on p. 1373). Chemische Berichte 1966, vol. 99, p. 1368-1383 describes a process for preparing 2,2,5,5-tetramethyl-1,4-dioxa-2,5-disilacyclohexane by converting (acetoxy-methyl)ethoxydimethylsilane by heating it with a large excess of methanol in the presence of p-toluenesulfonic acid (p-TsOH) to give ethoxy(hydroxymethyl)dimethylsilane, neutralizing the primary product and then distilling gradually with elimination of ethanol (reaction II):

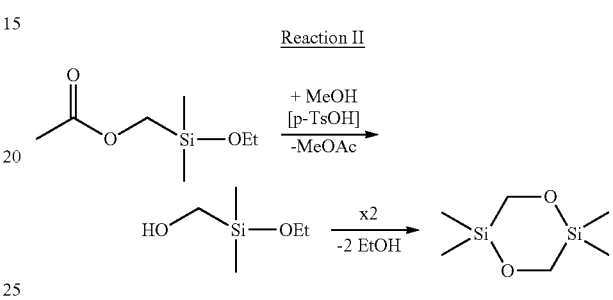

Reaction II

This process, however, is not economical due to only poor space-time yields, since more than ⅔ of the reaction volume consists of methanol and since the ethanol elimination, to suppress by-product formation, requires maintenance of a temperature of less than 100° C. At these temperatures, the ethanol, as reported explicitly by the cited reference, can be eliminated only gradually. If the reaction conditions are not controlled strictly, compounds which contain ether groups and have the structural unit Si—$CH_2$—O—$CH_2$—Si are formed under the acidic reaction conditions, and these contaminate the product. In addition, it is necessary to pass through an intermediate, in this case ethoxy(hydroxymethyl)-dimethylsilane, which constitutes an additional operating step. Moreover, Chemische Berichte 1966, vol. 99, p. 1368-1383 states that, after the distillative removal of the methyl acetate, a neutralization step is conducted with potassium hydroxide and $CO_2$ before the actual product, 2,2,5,5-tetramethyl-2,5-disila-1,4-dioxane, is obtained, which additionally makes the process laborious.

The reference Organosilicon Chemistry, Scientific Communications, Prague, 1965, p. 120-124 shows basically the same reaction route in the form of reaction equations, but does not contain any working or procedural instructions which would enable one skilled in the art to comprehend the reaction sequence shown therein or to isolate a product. p-Toluenesulfonic acid is likewise named as a catalyst in this reference, which is why the problem of ether formation as a by-product in the case of this reaction route must inevitably likewise occur.

The siloxacycles 2,2,5,5-Tetramethyl-1,4-dioxa-2,5-disilacyclohexane, 2,5-dimethyl-2,5-diphenyl-1,4-dioxa-2,5-disilacyclohexane and 2,2,5,5-tetraphenyl-1,4-dioxa-2,5-disilacyclohexane were prepared by condensation of (hydroxymethyl)dimethylsilane, (hydroxymethyl)methylphenylsilane and (hydroxymethyl)diphenylsilane respectively, with elimination of hydrogen, as reported in Zeitschrift für Naturforschung B, 1983, vol. 38, p. 190-193. Since the reacting COH and SiH groups are in the same compound and hence are inseparable during reactant storage, the silicon hydride used as a reactant can, however, start this reaction at any time in an uncontrolled manner if it comes into contact, for example, with catalytic traces of bases. The preparation of any great amounts of silanes having both an Si—H group and a carbinol group is therefore very hazardous and can be implemented on the industrial scale only with a high level of complexity, if at all.

Moreover, the specialist literature describes various methods for transesterification of silanes bearing an acyloxyalkyl group.

DE 1 251 961 B describes the preparation of cyclic silane compounds whose structure can be represented by the formula *—O—R'—SiR"$_2$—* where * is the point of ring closure and R' is a divalent hydrocarbyl radical which connects the silicon and oxygen atoms via at least three carbon atoms. This involves subjecting an ester of the structure acyl-O—R'—SiR"$_2$—OR''' to a transesterification reaction with an alcohol. If the thus prepared compounds of the structure *—O—R'—SiR"$_2$—* are reacted analogously to reaction I with silicone oils, the products formed, however, have a comparatively high organic component since R' has at least three carbon atoms, which is disadvantageous with regard to properties such as flame retardancy of the successor products.

Union Carbide has described, in several applications (see EP 129 121 A1, EP 120 115 A1, EP 107 211 A2, EP 106 062 A2, EP 93 806 A1, EP 73 027 A2 and EP 49 155 A2), the preparation of acyclic products having repeat units of the structure *[O—R'—SiR"$_2$—]$_p$* (*=end groups or undefined groups). This involves subjecting an ester of the structure acyl-O—R'—SiR"$_2$—OR''' to a transesterification reaction with elimination of an ester acyl-OR''', which is distilled out of the reaction mixture, the chain length distribution p of the product being controlled by the extent to which the transesterification is driven, and it is possible to add, as regulators to limit the extent of transesterification, high-boiling esters such as ethyl benzoate, methyl benzoate or ethyl laurate, which bring about blocking of the * end groups of the product by incorporating the acyl radical and the alkoxy radical of the high-boiling ester added into the product as * end groups. However, the preparation of cyclic compounds which could be isolated or purified, for example, by distillation has not been described.

The preparation of homocondensates of (hydroxymethyl)-silanes is also described in DE 44 07 437 A1. However, the document describes only how transesterification of (acyloxymethyl)silanes with alcohols gives an inhomogeneous mixture of linear or branched condensates.

SUMMARY OF THE INVENTION

The invention provides a process for preparing silaoxacycles of the general formula I

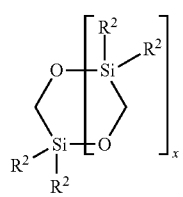

(I)

in which compounds of the general formula II

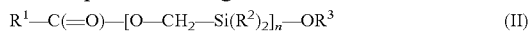

(II)

are converted in the presence of a catalyst which is selected from a metal or a compound of a metal of groups 3 to 15 and the lanthanoids of the Periodic Table of the Elements according to IUPAC notation, where x represents integers greater than or equal to 0,
n represents integers greater than or equal to 1,
$R^1$ is hydrogen or a hydrocarbyl radical which is unsubstituted or substituted by one or more $Q^1$ groups and may be interrupted by one or more heteroatoms, or an $OR^3$ group,
$R^2$ is hydrogen or a hydrocarbyl radical which is unsubstituted or substituted by one or more $Q^1$ groups and may be interrupted by one or more heteroatoms, or an $OR^4$ group,
$R^3$ is a hydrocarbyl radical which is unsubstituted or substituted by one or more $Q^1$ groups and may be interrupted by one or more heteroatoms,
$R^4$ is a hydrocarbyl radical which is unsubstituted or substituted by one or more $Q^1$ groups and may be interrupted by one or more heteroatoms, or a $CH_2Si(R^5)_{3-q}\{OCH_2Si(R^5)_{3-r}[OCH_2Si(R^5)_2(OR^3)]_r\}_q$ group,
q represents integers selected from 0, 1, 2 and 3,
r represents integers selected from 0, 1, 2 and 3,
$R^5$ is hydrogen or a hydrocarbyl radical which is unsubstituted or substituted by one or more $Q^1$ groups and may be interrupted by one or more heteroatoms, or an $OR^3$ group, and
$Q^1$ is a monovalent, divalent or trivalent heteroatom-containing radical,
where $R^1, R^2, R^3, R^4, R^5$ and $Q^1$ may be joined to one another so as to form one or more rings.

DETAILED DESCRIPTION OF THE PREFERRED EMBODIMENTS

The process is efficient and economic. By virtue of the process, the silaoxacycles of the general formula I can be made available without further purification in a purity which allows direct further use, for example according to the above reaction I.

It has been found that, surprisingly, the desired silaoxacycles can be prepared easily in a robust process and in high purity when silanes having acyloxymethyl and alkoxy groups are subjected to a transesterification in a particular manner.

The compounds of the general formula II and the catalysts can each be used in a mixture or as a pure substance. The silaoxacycles of the general formula I can likewise be obtained as a mixture or as a pure substance. Identical or different compounds of the general formula II or identical or different catalysts can be added successively in a plurality of steps.

Preferably, at least one compound of the general formula I is isolated from the reaction mixture. The isolation of the compound of the formula I from the reaction mixture is preferably accomplished by distillation, in which case the compound of the general formula I is distilled over as a distillate.

In the process, a by-product of the general formula III

(III)

is generally likewise removed, for example by distillation, in which case the by-product of the general formula III, according to the choice of $R^1$ and $R^3$ radicals, can be obtained as a distillate or as a distillation residue.

x preferably assumes values from 1 to 30, more preferably values from 1 to 3, and most preferably the value of 1. x may assume, for example, the values of 1, 2, 3, 4, 5, 6, 7, 8, 9 or 10.

n preferably assumes values from 1 to 30, more preferably values from 1 to 3, and most preferably the value of 1. n may assume, for example, the values of 1, 2, 3, 4, 5, 6, 7, 8, 9 or 10.

$R^1$ is, for example, a hydrogen atom or a linear or branched, saturated or mono- or polyunsaturated hydrocarbyl radical which is cyclic or acyclic or contains a plurality of cycles or—when $R^1$ is an $OR^3$ group—a hydrocarbyloxy radical. $R^1$ is preferably a hydrogen atom or a $C_1$-$C_{40}$ alkyl radical, a $C_6$-$C_{40}$ aryl radical, a $C_7$-$C_{40}$ alkylaryl radical or a $C_7$-$C_{40}$ arylalkyl radical. $R^1$ is preferably a hydrogen atom, a $C_1$-$C_{20}$ alkyl radical, a $C_6$-$C_{20}$ aryl radical, a $C_7$-$C_{20}$ alkylaryl radical or a $C_7$-$C_{20}$ arylalkyl radical. $R^1$ is more preferably a hydrogen atom, a $C_1$-$C_{12}$ alkyl radical, a $C_6$-$C_{12}$ aryl radical, a $C_7$-$C_{12}$ alkylaryl radical or a $C_7$-$C_{12}$ arylalkyl radical. $R^1$ preferably contains zero to four heteroatoms, especially zero heteroatoms. $R^1$ is preferably unsubstituted. $R^1$ most preferably consists exclusively of carbon and hydrogen atoms or is a hydrogen atom. Examples of $R^1$ are hydrogen, methyl, ethyl, n-propyl, isopropyl, n-butyl, isobutyl, sec-butyl, tert-butyl, n-pentyl, tert-pentyl, n-hexyl, n-heptyl, 1-ethylpentyl, n-octyl, n-nonyl, n-decyl, n-undecyl, n-tridecyl, n-pentadecyl, n-heptadecyl, n-nona-decyl, phenyl, benzyl, 2-methylphenyl, 3-methylphenyl, and 4-methylphenyl.

$R^2$ is, for example, a hydrogen atom or a linear or branched, saturated or mono- or polyunsaturated hydrocarbyl radical which is cyclic or acyclic or contains a plurality of cycles or—when $R^2$ is an $OR^4$ group—a hydrocarbyloxy radical. $R^2$ is preferably a hydrogen atom, a $C_1$-$C_{40}$ alkyl radical, a $C_6$-$C_{40}$ aryl radical, a $C_7$-$C_{40}$ alkylaryl radical, a $C_7$-$C_{40}$ arylalkyl radical, a $C_1$-$C_{40}$ alkoxy radical, a $C_2$-$C_{40}$ (alkoxy)alkoxy radical, a $C_6$-$C_{40}$ aryloxy radical, a $C_7$-$C_{40}$ arylalkoxy radical or a $C_7$-$C_{40}$ alkylaryloxy radical. $R^2$ is more preferably a $C_1$-$C_{20}$ alkyl radical, a $C_6$-$C_{20}$ aryl radical, a $C_7$-$C_{20}$ alkylaryl radical or a $C_7$-$C_{20}$ arylalkyl radical, a $C_1$-$C_{20}$ alkoxy radical, a $C_2$-$C_{20}$ (alkoxy)alkoxy radical, a $C_6$-$C_{20}$ aryloxy radical, a $C_7$-$C_{20}$ arylalkoxy radical or a $C_7$-$C_{20}$ alkylaryloxy radical. $R^2$ is most preferably a $C_1$-$C_{12}$ alkyl radical, a $C_6$-$C_{12}$ aryl radical, a $C_7$-$C_{12}$ alkylaryl radical or a $C_7$-$C_{12}$ arylalkyl radical, a $C_1$-$C_{12}$ alkoxy radical, a $C_2$-$C_{12}$ (alkoxy)alkoxy radical, a $C_6$-$C_{12}$ aryloxy radical, a $C_7$-$C_{12}$ arylalkoxy radical or a $C_7$-$C_{12}$ alkylaryloxy radical. $R^2$ preferably contains zero to four heteroatoms, more preferably zero or one heteroatom, and most preferably zero heteroatom when $R^2$ is not $OR^4$, and preferably one to two oxygen atoms, especially one oxygen atom, when $R^2$ is $OR^4$. $R^2$ is preferably unsubstituted or substituted by one alkoxy group, especially unsubstituted.

Most preferably, $R^2$ consists exclusively of carbon and hydrogen atoms or of carbon and hydrogen atoms and one oxygen atom; in the latter case, this oxygen atom is preferably bonded to the silicon atom. Examples of $R^2$ are methyl, ethyl, vinyl, allyl, ethynyl, propargyl, 1-propenyl, 1-methylvinyl, methallyl, phenyl, benzyl, ortho-, meta- or para-tolyl, methoxy, ethoxy, 2-methoxyethoxy, 2-methoxy-1-methylethoxy, n-propoxy, iso-propoxy, n-butoxy, isobutoxy, sec-butoxy, tert-butoxy, tert-pentoxy, n-hexoxy, 2-ethylhexoxy, n-octoxy, n-decoxy, n-dodecoxy, n-tetradecoxy, n-octadecoxy, n-eicosoxy, phenoxy or benzyloxy.

$R^3$ is, for example, a linear or branched, saturated or mono- or polyunsaturated hydrocarbyl radical which is cyclic or acyclic or contains a plurality of cycles. $R^3$ is preferably a $C_1$-$C_{40}$ alkyl radical, a $C_6$-$C_{40}$ aryl radical, a $C_7$-$C_{40}$ alkylaryl radical, a $C_7$-$C_{40}$ arylalkyl radical or a $C_2$-$C_{40}$ (alkoxy)alkyl radical. $R^3$ is preferably a $C_1$-$C_{20}$ alkyl radical, a $C_6$-$C_{20}$ aryl radical, a $C_7$-$C_{20}$ alkylaryl radical, a $C_7$-$C_{20}$ arylalkyl radical or a $C_2$-$C_{20}$ (alkoxy)alkyl radical. $R^3$ is more preferably a $C_1$-$C_{12}$ alkyl radical, a $C_6$-$C_{12}$ aryl radical, a $C_7$-$C_{12}$ alkylaryl radical, a $C_7$-$C_{12}$ arylalkyl radical or a $C_2$-$C_{12}$ (alkoxy)alkyl radical. $R^3$ preferably contains zero to four heteroatoms, more preferably zero or one heteroatom, and most preferably zero heteroatoms. $R^3$ is preferably unsubstituted or substituted by one alkoxy group, especially unsubstituted. $R^3$ more preferably consists exclusively of carbon and hydrogen atoms or of carbon and hydrogen atoms and one oxygen atom, this oxygen atom being part of an ether group, i.e. bonded to two carbon atoms. Examples of $R^3$ are methyl, ethyl, 2-methoxyethyl, 1-methyl-2-methoxyethyl, n-propyl, isopropyl, n-butyl, isobutyl, sec-butyl, tert-butyl, n-pentyl, tert-pentyl, n-hexyl, 2-ethylhexyl, n-octyl, n-decyl, n-dodecyl, n-tetradecyl, n-hexadecyl, n-octadecyl, n-eicosyl, phenyl or benzyl.

$R^4$ is, for example, a linear or branched, saturated or mono- or polyunsaturated hydrocarbyl radical which is cyclic or acyclic or contains a plurality of cycles. $R^4$ is preferably a $C_1$-$C_{40}$ alkyl radical, a $C_6$-$C_{40}$ aryl radical, a $C_7$-$C_{40}$ alkylaryl radical, a $C_7$-$C_{40}$ arylalkyl radical or a $C_2$-$C_{40}$ (alkoxy)alkyl radical or a $CH_2Si(R^5)_{3-q}\{OCH_2Si(R^5)_{3-r}-[OCH_2Si(R^5)_2(OR^3)]_r\}_q$ group. At least one $R^5$ group is preferably an $OR^3$ group when q or r is 0. $R^4$ is preferably a $C_1$-$C_{20}$ alkyl radical, a $C_6$-$C_{20}$ aryl radical, a $C_7$-$C_{20}$ alkylaryl radical, a $C_7$-$C_{20}$ arylalkyl radical or a $C_2$-$C_{20}$ (alkoxy)-alkyl radical. $R^4$ is more preferably a $C_1$-$C_{12}$ alkyl radical, a $C_6$-$C_{12}$ aryl radical, a $C_7$-$C_{12}$ alkylaryl radical, a $C_7$-$C_{12}$ arylalkyl radical or a $C_2$-$C_{12}$ (alkoxy)alkyl radical. $R^4$ preferably contains zero to four heteroatoms, preferably zero or one heteroatom, and most preferably zero heteroatoms. $R^4$ is preferably unsubstituted or substituted by one alkoxy group, especially unsubstituted. $R^4$ most preferably consists exclusively of carbon and hydrogen atoms or of carbon and hydrogen atoms and one oxygen atom, in which case this oxygen atom is part of an ether group, i.e. is bonded to two carbon atoms. Examples of $R^4$ are methyl, ethyl, 2-methoxyethyl, 1-methyl-2-methoxyethyl, n-propyl, isopropyl, n-butyl, isobutyl, sec-butyl, tert-butyl, n-pentyl, tert-pentyl, n-hexyl, 2-ethylhexyl, n-octyl, n-decyl, n-dodecyl, n-tetradecyl, n-hexadecyl, n-octadecyl, n-eicosyl, phenyl or benzyl.

$R^5$ is, for example, a hydrogen atom or a linear or branched, saturated or mono- or polyunsaturated hydrocarbyl radical which is cyclic or acyclic or contains a plurality of cycles, or when $R^5$ is an $OR^3$ group, is a hydrocarbyloxy radical. $R^5$ is preferably a hydrogen atom, a $C_1$-$C_{40}$ alkyl radical, a $C_6$-$C_{40}$ aryl radical, a $C_7$-$C_{40}$ alkylaryl radical, a $C_7$-$C_{40}$ arylalkyl radical, a $C_1$-$C_{40}$ alkoxy radical, a $C_2$-$C_{40}$ (alkoxy)alkoxy radical, a $C_6$-$C_{40}$ aryloxy radical, a $C_7$-$C_{40}$ arylalkoxy radical or a $C_7$-$C_{40}$ alkylaryloxy radical. $R^5$ is more preferably a $C_1$-$C_{20}$ alkyl radical, a $C_6$-$C_{20}$ aryl radical, a $C_7$-$C_{20}$ alkylaryl radical or a $C_7$-$C_{20}$ arylalkyl radical, a $C_1$-$C_{20}$ alkoxy radical, a $C_2$-$C_{20}$ (alkoxy)alkoxy radical, a $C_6$-$C_{20}$ aryloxy radical, a $C_7$-$C_{20}$ arylalkoxy radical or a $C_7$-$C_{20}$ alkylaryloxy radical. $R^5$ is most preferably a $C_1$-$C_{12}$ alkyl radical, a $C_6$-$C_{12}$ aryl radical, a $C_7$-$C_{12}$ alkylaryl radical or a $C_7$-$C_{12}$ arylalkyl radical, a $C_1$-$C_{12}$ alkoxy radical, a $C_2$-$C_{12}$ (alkoxy)alkoxy radical, a $C_6$-$C_{12}$ aryloxy radical, a $C_7$-$C_{12}$ arylalkoxy radical or a $C_7$-$C_{12}$ alkylaryloxy radical. $R^5$ preferably contains zero to four heteroatoms, more preferably zero or one heteroatom, and most preferably zero heteroatoms when $R^5$ is not $OR^3$, and more preferably one to two oxygen atoms, especially one oxygen atom, when $R^5$ is $OR^3$. $R^5$ is preferably unsubstituted or substituted by one alkoxy group, especially unsubstituted. $R^5$ more preferably consists exclusively of carbon and hydrogen atoms or of carbon and hydrogen atoms and one oxygen atom; in the latter case, this oxygen atom is preferably bonded to the silicon atom. Examples of $R^5$ are methyl, ethyl, vinyl, allyl, ethynyl, propargyl, 1-propenyl, 1-methylvinyl, methallyl, phenyl, benzyl, ortho-, meta- or para-tolyl, methoxy, ethoxy, 2-methoxyethoxy, 2-methoxy-1-methylethoxy, n-propoxy, isopropoxy, n-butoxy, isobutoxy, sec-butoxy, tert-butoxy, tert-pentoxy, n-hexoxy, 2-ethylhexoxy, n-octoxy, n-decoxy, n-dodecoxy, n-tetradecoxy, n-octadecoxy, n-eicosoxy, phenoxy or benzyloxy.

q preferably assumes the values of 0, 1 or 2, more preferably 0 or 1, and most preferably 0.

r preferably assumes the values of 0, 1 or 2, more preferably 0 or 1, and most preferably 0.

$Q^1$ is preferably a halogen atom, for example a fluorine, chlorine, bromine or iodine atom, a hydrocarbyloxy group, for example a $C_1$-$C_{40}$ alkoxy group or a $C_6$-$C_{40}$ aryloxy group, an acyl group, for example an aliphatic $C_1$-$C_{40}$ acyl group, or an aromatic $C_7$-$C_{40}$ acyl group, a hydrocarbyl sulfide group, for example a $C_1$-$C_{40}$ alkyl sulfide group or a $C_6$-$C_{40}$ aryl sulfide group, a cyano group or a nitro group.

In a particularly preferred combination, the above-defined groups are selected such that the $R^1$ radical is a hydrogen atom, a methyl group or an ethyl group, the $R^2$ radicals are each independently methyl, methoxy or ethoxy groups, especially methyl groups, the $R^3$ radical is a methyl or ethyl group, n assumes integer values from 1 to 3, especially 1, and x assumes integer values from 1 to 3, especially 1.

The structural unit $[O-CH_2-Si(R^2)_2]_n$ in the general formula II may be linear or branched. If, for example, the compounds of the general formula II selected were compounds where $R^1$=Me, $R^2$=OMe and $OR^3$=OMe, the general formula II may represent structures including the following:

n=1:

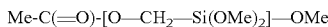
Me-C(=O)-[O—CH$_2$—Si(OMe)$_2$]—OMe n=2 (linear):

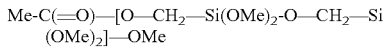
Me-C(=O)—[O—CH$_2$—Si(OMe)$_2$-O—CH$_2$—Si(OMe)$_2$]—OMe n=3 (linear):

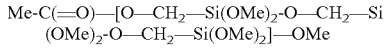
Me-C(=O)—[O—CH$_2$—Si(OMe)$_2$-O—CH$_2$—Si(OMe)$_2$-O—CH$_2$—Si(OMe)$_2$]—OMe n=3 (branched):

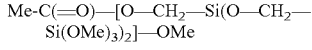
Me-C(=O)—[O—CH$_2$—Si(O—CH$_2$—Si(OMe)$_3$)$_2$]—OMe n=4 (branched, selected example):

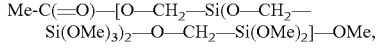
Me-C(=O)—[O—CH$_2$—Si(O—CH$_2$—Si(OMe)$_3$)$_2$—O—CH$_2$—Si(OMe)$_2$]—OMe, where the structural units in square brackets always have the empirical formula of $[O-CH_2-Si(OMe)_2]_n$ with the particular specified value of n.

Compounds of the general formula II are, for example, when n=1, preparable by a process as described in Monatshefte für Chemie 2003, vol. 134, p. 1081-1092 (see the section "General Procedure for the Synthesis of 1-4" in the reference at p. 1090); instead of the methacrylic acid described therein, it is also possible to use another carboxylic acid of the formula $R^1$COOH. If, instead of a carboxylic acid, a dry carboxylic salt is used, the azeotropic step described therein can be omitted; if a carboxylic acid or salt thereof which does not have a group sensitive to polymerization under free-radical conditions is used, the stabilizer (4,4'-bis-methylene(2,6-di-tert-butylphenol)) described therein can also be omitted.

Compounds of the general formula II in which n has values greater than or equal to 2 can be produced, for example, in a preceding run of the execution of the process according to the invention, or by the processes described in EP 129 121 A1, EP 120 115 A1, EP 107 211 A2, EP 106 062 A2, EP 93 806 A1, EP 73 027 A2 and EP 49 155 A2 from compounds of the general formula II which have the value of 1 for n.

The invention also provides the compounds of the general formula IV

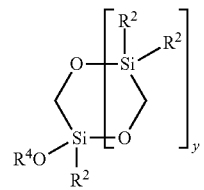

(IV)

where $R^2$ and $R^4$ may assume the same definitions as defined above and
y may assume integer values greater than or equal to 1.

The above-described preferred definitions for $R^2$ and $R^4$ likewise apply to the general formula IV.

y preferably assumes values from 1 to 30, more preferably values from 1 to 3, and most preferably the value of 1. y may assume, for example, the values of 1, 2, 3, 4, 5, 6, 7, 8, 9 or 10.

The compounds of the general formula IV are a selection from compounds of the general formula I, wherein at least one of the $R^2$ radicals in the latter is selected from $OR^4$ groups and the silaoxacycle has an at a least 6-membered ring.

The process is executed in the presence of at least one metal catalyst wherein at least one metal is selected from groups 3 to 15 (according to IUPAC notation) of the Periodic Table of the Elements or from the lanthanides, namely cerium, praseodymium, neodymium, samarium, europium, gadolinium, terbium, dysprosium, holmium, erbium, thulium, ytterbium and lutetium; promethium is less preferred since only radioactive isotopes thereof exist. The lightest metals of groups 3 to 15 are aluminum, scandium, titanium, vanadium, chromium, manganese, iron, cobalt, nickel, copper, zinc, gallium and germanium. Moderately heavy metals of groups 3 to 15 are yttrium, zirconium, niobium, molybdenum, ruthenium, rhodium, palladium, silver, cadmium, indium, tin and antimony; technetium is less preferred since only radio-active isotopes thereof exist. Heavier metals of groups 3 to 15 are lanthanum, hafnium, tantalum, tungsten, rhenium, osmium, iridium, platinum, gold, mercury, thallium, lead and bismuth.

For the delimitation of the metals from the nonmetals, the delimitation as documented in the chemical lexicon Römpp Online, version 3.6, in the article under "Periodensystem" [Periodic Table], last updated August 2006, is used.

In contrast to p-toluenesulfonic acid or sulfuric acid, which were described as catalysts in Chemische Berichte 1966, vol. 99, p. 1368-1383, the problem of formation of by-products containing ether groups (structural unit: Si—CH$_2$—O—CH$_2$—Si) in the case of use of metal catalysts is much less marked or absent, which allows a much simpler and more robust reaction regime giving a purer product. In contrast to calcium oxide, the catalysts chosen give much purer products, and additionally generally in much better yields.

Preference is given to using compounds of metals or metals of groups 4 to 15 (according to IUPAC notation) of the Periodic Table of the Elements, preferably metals or compounds of titanium, iron, cobalt, nickel, zinc, aluminum, tin, lead and/or bismuth, more preferably tin or compounds thereof or titanium or compounds thereof.

The metal catalysts can be used, for example, as a pre-catalyst which can produce the actual active catalyst form in its active form or in a dormant form. The metals can be used, for example, as the element, in which case the actual catalysts can be prepared in situ through additions, for example oxidizing agents, or the surfaces of the metals, which may be present, for example, in oxidic form, can act catalytically or release catalytically active metal or compounds thereof to the reaction mixture, or it is possible to use compounds of the metals. The metal compounds used may, for example, be dimethyltin oxide, dilaurate, dineodecanoate, dioctanoate, di-2-ethylhexanoate, diacetate, di(acetylacetonate), maleate, oxalate, dichloride, hydrogenphosphite, sulfide or bis(octylmaleate), dibutyl-tin oxide, dilaurate, dineodecanoate, dioctanoate, di-2-ethylhexanoate, diacetate, di(acetylacetonate), maleate, oxalate, dichloride, hydrogenphosphite, sulfide or bis(octylmaleate), dioctyltin oxide, dilaurate, dineodecanoate, dioctanoate, di-2-ethylhexanoate, diacetate, di(acetylacetonate), maleate, oxalate, dichloride, hydrogenphosphite, sulfide or bis(octylmaleate), or tin(II) oxide, dilaurate, dineodecanoate, dioctanoate, di-2-ethylhexanoate, diacetate, di(acetylacetonate), maleate, oxalate, dichloride, hydrogenphosphite, sulfide or bis(octylmaleate), tetrabutyldilauroyloxydistannoxane, butyl- or octyltin trilaurate, trineodecanoate, trioctanoate, tri(2-ethylhexanoate), triacetate, tri(acetylacetonate), *1,5-maleate, trichloride, *1,5-sulfide, tris(octylmaleate), (chloride)(dihydroxide) or acid, tetrabutyl- or tetraoctyltin, titanium(IV) iso-propoxide, titanium(IV) n-butoxide, zinc ricinoleate, octanoate, di(acetylacetonate) or oxalate, bismuth(III) methanesulfonate, octanoate, citrate or oxide, iron(III) acetylacetonate, cobalt(II) acetylacetonate, nickel(II) acetylacetonate, aluminum(III) isopropoxide or aluminum lactate.

The catalysts are preferably used in equivalents of at least 0.001 mmol, more preferably at least 0.01 mmol, and most preferably at least 0.1 mmol, and preferably at most 0.9 mol, more preferably at most 0.2 mol, and most preferably at most 0.1 mol, based on 1 molar equivalent of the compounds of the general formula II used in total in the process. In the case of supported catalysts, the equivalents thereof are calculated using the amount of active sites. The amount of active sites may correspond, for example, to the amount of metal atoms in the metals being considered in accordance with the invention for the catalysts.

The catalysts may be used, for example, in solution, in the liquid phase, in the solid phase, in the gas phase, in supercritical media, in substance (neat), and in liquid, solid, gaseous, homogeneous or heterogeneous or supported form. The supports used may, for example, be silica gel or alumina. The catalysts may be used in combination with cocatalysts, promoters, moderators or catalyst poisons. Promoters can enhance the action of catalysts. Catalyst poisons can attenuate the action of catalysts or suppress unwanted catalytic effects. The catalysts may be used, for example, directly in the reaction vessel, or the reaction mixture may, for example, be conducted once or repeatedly or in a circulating manner over the catalysts.

The reaction through which the compounds of the general formula II react to give compounds of the general formula I can be executed, for example, in the gas phase, in the liquid phase, in the solid phase, in the supercritical state, in supercritical media, in solution or in substance. Preference is given to executing the process in the liquid phase, in solution or in substance, preferably in the liquid phase, preferably in substance, more preferably in the liquid phase and in substance.

The process can be performed over a wide temperature range, for example at least 0° C., preferably at least 30° C., more preferably at least 40° C., and most preferably at least 50° C., and, for example, at most 400° C., preferably at most 300° C., more preferably at most 250° C., and most preferably at most 200° C.

The process can be executed over a wide pressure range, for example at least 0.1 Pa, preferably at least 1 Pa, more preferably at least 10 Pa, and most preferably at least 100 Pa and, for example, at most 500 MPa, preferably at most 10 MPa, more preferably at most 1 MPa, and most preferably at most 500 kPa absolute. In a particularly preferred embodiment, the process is executed at atmospheric pressure, which, according to the ambient conditions, is generally within a range between 90 and 105 kPa absolute.

The process can be executed continuously or batchwise. In the batchwise embodiment, the process can be executed, for example, in a cascade reactor or in a stirred tank. In the continuous embodiment, the process can be executed, for example, in a tubular, delay, circulation or cascade reactor, or a dynamic or static mixer.

If compounds of the general formula II in which n has a particular value or particular values are used as the reactant in the process, in the course of execution of the process, compounds of the general formula IIa may occur

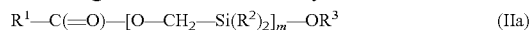 (IIa)

where $R^1$, $R^2$ and $R^3$ may assume the definitions given above and m may assume integer values greater than or equal to 1, and in which m has values which differ from the values for n as possessed by the compounds of the general formula II used in each case.

If, in the process, for example, the particularly preferred compounds of the general formula II in which n has the value of 1 are used as the reactant, in the course of execution of the process, compounds of the general formula IIa in which m has values greater than or equal to 2 may occur.

m may assume, for example, values of 2 to 100, for example 2, 3, 4, 5, 6, 7, 8, 9 or 10. If compounds of the general formula II in which n assumes values other than 1 are used as the reactant, m may, for example, also assume the value of 1.

The structural unit $[O—CH_2—Si(R^2)_2]_m$ in the general formula IIa may be linear or, if at least one of the $R^2$ radicals has been selected from radicals of the structure $OR^4$, branched, in which case $R^4$ may assume the definitions given above. If, for example, the compound of the general formula II chosen was (acetoxymethyl)trimethoxysilane (i.e. the choices were: $R^1$=Me, $R^2$=OMe, $OR^3$=OMe, n=1), in the course of the reaction, for example, compounds including the following compounds of the general formula IIa may occur:

m=2 (linear):

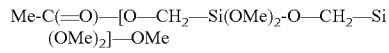

m=3 (linear):

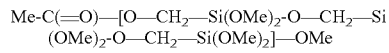

m=3 (linear):

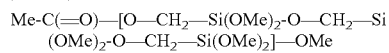

m=3 (branched):

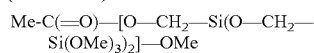

m=4 (branched, selected example):

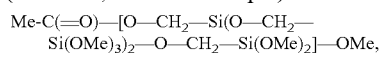

where the structural units in square brackets always have the empirical formula of $[O—CH_2—Si(OMe)_2]_m$ with the particular value specified for m.

The compounds of the general formula IIa can be converted further in the process according to the invention to compounds of the general formula I. In this case, compounds of the general formula III may form as by-products.

The process can be executed, for example, under reflux or under distillative conditions, optionally under partial reflux, for example in a distillation apparatus, a thin-film or falling-film evaporator, optionally in a column with separating performance. For example, it is possible to distil one or more compounds of the general formula I, II or III out of the mixture.

In a first preferred embodiment, a compound of the formula III is distilled out and compounds of the general formulae I, IIa and II are at first kept partly or fully in the reaction mixture, for example via reflux, and, once compound of the general formula III has been partly or fully distilled off, distillation of the product of the general formula I into a receiver is commenced, while keeping compound of the general formulae IIa and II partly or fully in the reaction mixture, for example via reflux.

In a second preferred embodiment, the compounds of the general formulae I and III are distilled out of the mixture and the compounds of the general formulae II and IIa are kept partly or fully in the mixture, for example via reflux.

In a third preferred embodiment, the procedure is as in the second preferred embodiment and the distillate comprising compounds of the general formulae I and III is subjected to a redistillation.

Compounds of the general formulae II and IIa are, during the execution of distillative process steps, preferably converted further to compounds of the general formula I, forming, for example, compounds of the general formula III as by-products, which are preferably removed, for example in the same or a subsequent distillation step.

The distillates obtained in the preferred embodiments are partly or fully condensed. Preference is given to selecting catalysts used with regard to their vapor pressure such that they and their compounds which form, for example, in the catalytic cycle or in other reactions preferably remain in the reaction mixture in distillative process steps, which can be achieved, for example, by using salt-type catalysts or catalysts which, in their use form or in their active form or in their dormant form, have a higher molar mass than the products of the general formula I and/or optionally III. The catalysts preferably catalyze the reaction of compound of the general formula II to give compounds of the general formula I and optionally IIa and/or III, and/or the reaction of compounds of the general formula IIa to give I and optionally III during the execution of the distillative process step in addition. The reaction of compound of the general formula II to give compounds of the general formula I and optionally IIa and/or III may be an equilibrium reaction. Preference is given to employing the first, second or third preferred embodiment of the process, such that the products of the general formula I or III or both are removed from the equilibrium, preferably in the presence of catalysts, and the reactant of the general formula II used is converted to an extent of preferably at least 50 mol %, more preferably at least 70 mol %, especially preferably at least 90 mol %, based on the theoretically possible amount in total, to products of the general formula I.

Preference is given to using unconverted compounds of the general formula II and any compounds of the general formula IIa obtained in a new batch, which is preferably executed after the process according to the invention. It is likewise possible to use compounds of the general formula II or IIa, which may optionally originate from other sources, in the process according to the invention.

Before, during or after the execution of the process, the catalysts may form active or inactive, activatable, reactivatable or non-reactivatable species. Such species may have, for example, the following structural elements:

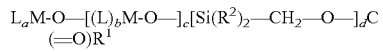

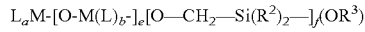

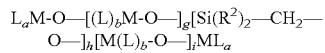

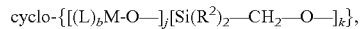

where M is a metal atom, L means ligands which, for example, can be introduced into the reaction mixture with the form of the catalyst used or can bind to the metal in situ, for example $OR^3$ groups, $OC(O)R^1$ groups, $R^2$ groups, carbonyl groups, $R^1$ groups or $C(O)R^1$ groups, a, b, c, e, g, h, i and k are integer values greater than or equal to 0, d, f and j are integer values greater than or equal to 1, and where the catalyst species may be linear or branched or cyclic or have several cycles, and where the symbols M, in the case of species having a plurality of metal atoms M, may be identical or different metallic elements.

The ligands L which can be introduced into the reaction mixture with the form of the catalyst used may, for example, be the groups named above as metal-bound groups in the catalysts described by way of example. In addition, further ligands L can be added to the reaction mixture, for example mono-, bi-, tri-, tetra-, penta- or hexadentate compounds and those of higher denticity, for example sulfur compounds, phosphorus compounds, carbon monoxide, cyanides, ethylenediamine, tetramethylethylene-diamine, ethylenediaminetetraacetate and salts thereof, citrates, acetylacetone and salts thereof or glyoximes or ethers, oligoethers or polyethers, for example polyethylene glycol or polypropylene glycol.

Catalysts used are preferably recovered in their active form used or in a reactivatable dormant form, and are preferably reused in the process according to the invention.

In the process, it is possible to add compounds which intervene in the course of the reaction, for example carboxylic acids and derivatives thereof or alcohols and derivatives thereof.

In the process, it is optionally possible to add alcohols of the structure $R^6OH$ where $R^6$ may assume the same definitions as $R^3$ as defined above. In this case, in the aforementioned formulae, the $OR^3$ and $OR^4$ groups may be partly or fully replaced by $OR^6$ groups, in which case alcohols of the structure $R^3OH$ or $R^4OH$ can be formed, and the $R^1$—C(=O)— groups in the aforementioned formulae may be replaced by hydrogen. If $R^6$ has more than one alcoholic OH function, it is possible for a plurality of such exchange reactions to take place, such that corresponding structures bridged via $R^6$ are formed.

In the process, it is optionally possible to add esters of the structure $R^7$—C(=O)—$OR^6$ where $R^6$ may assume the same definitions as defined above and $R^7$ may assume the same definitions as defined above for $R^1$. In this case, in the aforementioned formulae, the $OR^3$ and $OR^4$ groups may be partly or fully replaced by $OR^6$ groups and the $R^1$—C(=O)— groups may be partly or fully replaced by $R^7$—C(=O)— groups. If $R^7$ has further carboxylic acid functions which may be partly or fully esterified, or $R^6$ has further alcoholic OH functions which may be partly or fully esterified, it is possible for a plurality of such exchange reactions to take place, such that corresponding structures bridged via $R^7$ or via $R^6$ are formed.

In the process, it is optionally possible to add carboxylic acids of the structure $R^7$—C(=O)—OH where $R^7$ may assume the same definitions as defined above. In this case, in the aforementioned formulae, the $R^1$—C(=O)— groups may be partly or fully replaced by $R^7$—C(=O)— groups, and the OR³ and OR⁴ groups may be partly or fully replaced by OH groups. Si-bonded OH groups formed can also form corresponding siloxanes as a result. If $R^7$ has a plurality of C(=O)OH functions, it is possible for a plurality of such exchange reactions to take place, such that corresponding structures bridged via $R^7$ are formed.

In the process, it is optionally possible to use or add solvents or mixtures of solvents. Examples of usable solvents are optionally halogenated, for example chlorinated, or halogen-free hydrocarbons, ketones or ethers. If alcohols, esters or carboxylic acids are used as solvents, the effects described above for these substance classes may occur, which, if these effects are unwanted, can lead to a restriction of the solvent selection from these substance classes. The solvents may be saturated or unsaturated; unsaturated solvents preferably have aromatic unsaturation. Examples of usable solvents are isomers of $C_5$-$C_{40}$ hydrocarbons, for example cyclohexane, heptane, octane, iso-octane, nonane, decane, dodecane, benzene, toluene, ortho-, meta- or para-xylene or -cymene, cumene, ethylbenzene, diethylbenzene, or hydrocarbon mixtures, for example those from the Shellsol series from Shell or from the Hydroseal series from Total, $C_3$-$C_{40}$ ketones such as acetone, butanone, 2-pentanone, 3-pentanone, 3-methylbutanone, 4-methylpentan-2-one, cyclohexanone, ethers such as tetrahydrofuran, diethyl ether, tert-butyl methyl ether, tert-amyl methyl ether, diisopropyl ether, halogenated hydrocarbons such as chlorobenzene, ortho-, meta- or para-dichlorobenzene, or the isomers of trichlorobenzene.

Preference is given to using a minimum amount of solvent in the process: the mass of solvent, the total of all solvents, is preferably less than five times the mass of compounds of the general formula II used in total, preferably less than twice the amount, more preferably less than half the amount. In a particularly preferred embodiment, the process is executed without added solvents.

The presence of water in the reaction mixture can lead, for example, to the hydrolysis of Si-bonded OR³ and OR⁴ groups and to the hydrolysis of Si—OCH₂ structural units, in which case silanols and siloxanes can be formed as intermediates or end products. In addition, water can cause the hydrolysis of C(=O)—OC groups to the corresponding carboxylic acids and alcohols. Depending upon the catalyst used, water can also react with the catalyst, for example to form hydrates, hydroxo or oxo compounds, or oxides. Overall, water can, for example, influence the course of the reaction, the reaction rate, the product purity and the yield. One skilled in the art can easily determine, through suitable preliminary tests, which amounts of water cause which effects.

The process is preferably executed under inert conditions, preferably under a nitrogen or argon atmosphere. Solvents and reactants preferably used contain less than 10,000 ppm of water, more preferably less than 1000 ppm, and most preferably less than 200 ppm. Gases used, for example protective gases, preferably contain less than 10 000 ppm of water, more preferably less than 1000 ppm, and most preferably less than 200 ppm, and preferably less than 10,000 ppm of oxygen, more preferably less than 1000 ppm, and most preferably less than 200 ppm. Catalysts used preferably contain less than 10% water, more preferably less than 2%, and most preferably less than 0.5%.

Compounds of the general formula I prepared by the process according to the invention can, for example, be used directly as obtained, i.e. possibly in a mixture with compounds of the general formulae II, IIa, III, or with catalysts, promoters, catalyst poisons, co-reagents or solvents, for subsequent chemical reactions or other applications. The reaction products prepared can, however, also optionally be purified. Preference is given to distilling the compounds of the general formula I directly out of the reaction mixture which optionally still contains catalyst. The distillation of compounds of the general formula I can, as the case may be, be effected before, during (i.e. together with) or after the distillation of other compounds, for example compounds of the general formula II, IIa or III. Redistillation is an option. Compounds of the general formula I may, for example, be obtained in liquid form, or may solidify or crystallize. Preference is given to selecting catalysts, promoters or catalyst poisons, and workup steps, such that catalysts, promoters, catalyst poisons, co-reagents or solvents are present in the isolated product of the general formula I to an extent of less than 10%, preferably less than 1%, more preferably less than 0.1%. Skilled persons can easily find, through preliminary tests, the possible combinations of catalysts, promoters or catalyst poisons and workup or purification steps; instructions for catalysts, promoters, catalyst poisons, workup and purification steps have been mentioned above and can be found in the examples.

All above symbols in the above formulae are each defined independently of one another and may be the same or different in all formulae. Unless stated otherwise, the above percent figures are percentages by weight. Unless stated otherwise, yields stated in % of theory are based on the amount of silane used and have been calculated taking account of the stated purities of the respective products. In all formulae, the silicon atom is tetravalent. Unless stated otherwise, all pressure figures are absolute pressure figures. Unless stated otherwise, the definition of "heteroatom" encompasses all elements except carbon and hydrogen. In the case of what are called dialkyltin oxides, which are generally used in the form of poly(dialkylstannoxanes), the amounts reported were calculated on the basis of the specified formula unit of the dialkyltin oxide.

EXAMPLES

Example 1

2,2,5,5-Tetramethyl-2,5-disila-1,4-dioxacyclohexane (catalyst: dioctyltin oxide; reuse of the catalyst)

(a + b) (MeO)Si(Me)₂CH₂OC(O)Me ->

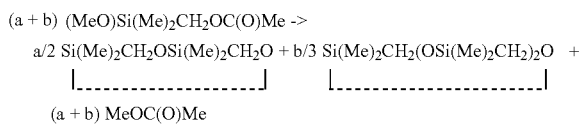

(a + b) MeOC(O)Me

Reaction

A mixture of 70.0 kg of (acetoxymethyl)dimethylmethoxysilane (431.4 mol) and 0.78 kg of dioctyltin oxide (2.2 mol) was heated to 120° C. under a nitrogen atmosphere. Within 3 hours, 17.4 kg of methyl acetate (234.9 mol) were distilled off therefrom using a column at 1 bar and a bottom temperature of 118-122° C. Thereafter, under reflux cooling, a dynamic vacuum was applied, which was increased to 60 mbar at a bottom temperature of 120° C. within 7 hours and then held at 60 mbar and at a bottom temperature of 117° C. for a further 7 hours. The methyl acetate formed and evaporated off was condensed on the pressure side of the vacuum pump. Thereafter, the reflux cooling was switched off and 29.2 kg of distillate were removed via a column at 55-75 mbar, bottom temperature 121° C. and top temperature 40-68° C. (product fraction). The product was obtained as a colorless liquid in high purity (2,2,5,5-tetramethyl-2,5-disila-1,4-dioxane, proportion in the product 97.1% (GC area %), corresponding to 160.8 mol, and 2,2,5,5,8,8-hexamethyl-2,5,8-trisila-1,4,7-trioxane, proportion in the product 2.1% (GC area %), corresponding to 2.3 mol; yield (total) 76% of theory). The isolated product contained only 0.3% (GC area %) of (acetoxymethyl)dimethylmethoxysilane, 0.1% (GC area %) of methyl acetate and 0.2 ppm of tin (calculated as metal). The bottoms contained catalyst.

Reuse of the Catalyst

Another 70.0 kg of (acetoxymethyl)dimethylmethoxysilane (431.4 mol) were added to the distillation bottoms under a nitrogen atmosphere, and the mixture was heated to 120° C. Within 2 hours, 14.8 kg of methyl acetate (199.8 mol) were distilled off therefrom using a column at 1 bar and bottom temperature 117-122° C. Thereafter, under reflux cooling, a dynamic vacuum was applied, which was increased to 120 mbar at a bottom temperature 120° C. within 4 hours and then held at 120 mbar and at a bottom temperature 119-120° C. for a further 9 hours. The methyl acetate formed and evaporated off was condensed on the pressure side of the vacuum pump (6.7 kg, 89.9 mol). Thereafter, the reflux cooling was switched off and 29.8 kg of distillate were removed using a column at 54-77 mbar, bottom temperature 119-122° C. and top temperature 46-60° C. (product fraction). The product was obtained as a colorless liquid in high purity (2,2,5,5-tetramethyl-2,5-disila-1,4-dioxane, proportion in the product 97.4% (GC area %), corresponding to 164.6 mol, and 2,2,5,5,8,8-hexamethyl-2,5,8-trisila-1,4,7-trioxane, proportion in the product 1.8% (GC area %), corresponding to 2.0 mol; yield (total) 78% of theory). The isolated product contained only 0.4% (GC area %) of (acetoxymethyl)dimethylmethoxysilane, 0.1% (GC area %) of methyl acetate and 0.1 ppm of tin (calculated as metal). The bottoms contained catalyst.

Example 1 shows that the catalyst can be reused with the same yield of product.

Example 2

2,2,5,5-Tetramethyl-2,5-disila-1,4-dioxacyclohexane (catalyst: dioctyltin oxide)

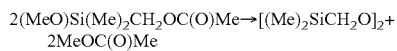

A mixture of 71.7 kg of (acetoxymethyl)dimethylmethoxysilane (441.9 mol) and 0.76 kg of dioctyltin oxide (2.1 mol) was heated to 120° C. under a nitrogen atmosphere. Within 3.5 hours, 22.5 kg of methyl acetate (303.7 mol) were distilled off therefrom using a column at 1 bar, in the course of which the bottom temperature was at first 115-124° C. for 1.5 hours and was then increased to 150° C. in the next 2 hours. Thereafter, under reflux cooling, a dynamic vacuum was applied, which was increased to 210 mbar at a bottom temperature of 145-150° C. within 6 hours. The methyl acetate formed and evaporated off was condensed on the pressure side of the vacuum pump (3.0 kg, 40.5 mol). Thereafter, the reflux cooling was switched off and 26.8 kg of distillate were removed using a column at 20-60 mbar, bottom temperature 118-123° C. and top temperature 58-75° C. (product fraction). The product (2,2,5,5-tetramethyl-2,5-disila-1,4-dioxane, 152.0 mol, 72% of theory, purity 99.2% (GC area %)) was obtained as a colorless liquid. It contained only 0.3% (GC area %) of (acetoxymethyl)dimethylmethoxysilane and 0.1% (GC area %) of methyl acetate. The catalyst remained in the bottoms.

Example 3

2,2,5,5-Tetramethyl-2,5-disila-1,4-dioxacyclohexane (catalyst: dibutyltin dilaurate)

A mixture of 36.5 g of (acetoxymethyl)dimethylmethoxysilane (225 mmol) and 1.6 g of dibutyltin dilaurate (2.5 mmol) was heated to 120° C. under a nitrogen atmosphere. Within 5 hours, 10.9 g of methyl acetate (147 mmol) were distilled off therefrom using a Widmer column at 1 bar and bottom temperature 116-121° C. Thereafter, under reflux cooling, a dynamic vacuum was applied, which was increased to 72 mbar at bottom temperature 120° C. within 1 hour and then held at 72 mbar and bottom temperature 120-125° C. for a further 4 hours. The methyl acetate formed and evaporated off was condensed in a cold trap at −78° C. (3.5 g, 47 mmol). Thereafter, the reflux cooling was switched off and 16.9 g of distillate were removed at 10 mbar, bottom temperature 122-124° C. and top temperature 39-40° C. (product fraction). The product (2,2,5,5-tetramethyl-2,5-disila-1,4-dioxane, 95.8 mmol, 85% of theory, purity 98.9% (GC area %)) was obtained as a colorless liquid. It contained no (acetoxymethyl)dimethylmethoxysilane, 0.2% (GC area %) of methyl acetate and <0.1 ppm of tin (calculated as metal). The bottoms contained catalyst.

Example 4

2,2,5,5-Tetramethyl-2,5-disila-1,4-dioxacyclohexane (catalyst: dibutyltin oxide)

A mixture of 100 g of (acetoxymethyl)dimethylmethoxysilane (616 mmol) and 750 mg of dibutyltin oxide (3.1 mmol) was heated to 120° C. under a nitrogen atmosphere. Within 100 minutes, 24.2 g of methyl acetate (327 mmol) were distilled off therefrom using a Vigreux column at 1 bar and bottom temperature 120° C. Thereafter, without reflux cooling, a dynamic vacuum was applied, which was increased to 70 mbar at bottom temperature 120° C. within 3 hours. The methyl acetate formed and evaporated off was condensed in a cold trap at −78° C. (17.9 g, 242 mmol). Thereafter, 50.3 g of distillate were removed at 15 mbar, bottom temperature 87-125° C. and top temperature 38-48° C. (product fraction); the main fraction was obtained at a stable top temperature 48° C./15 mbar. The product was obtained as a colorless liquid; it contained 98.8% (GC area %) of 2,2,5,5-tetramethyl-2,5-disila-1,4-dioxane, corresponding to 282 mmol (91% of theory). The product contained no (acetoxymethyl)dimethylmethoxysilane, 0.2% (GC area %) of methyl acetate and 0.5 ppm of tin (calculated as metal). The bottoms contained catalyst.

Example 5

2,5-Dimethoxy-2,5-dimethyl-2,5-disila-1,4-dioxacyclohexane (cis/trans mixture) (catalyst: dioctyl tin oxide)

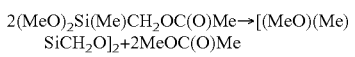

A mixture of 44.6 g of (acetoxymethyl)methyldimethoxysilane (250 mmol) and 0.45 g of dioctyltin oxide (1.25 mmol) was heated to 120° C. under a nitrogen atmosphere. Within 3 hours, 10.7 g of methyl acetate (144 mmol) were distilled off therefrom using a Widmer column at 1 bar and bottom temperature 86-117° C. Thereafter, under reflux cooling, a dynamic vacuum was applied, which was increased to 28 mbar at bottom temperature 120-135° C. within 5 hours. The methyl acetate formed and evaporated off was condensed in a cold trap at −78° C. (5.6 g, 76 mmol). Thereafter, the reflux cooling was switched off and 16.6 g of distillate were removed using a Widmer column at 0.4 mbar, bottom temperature 108-114° C. and top temperature 27° C. (product fraction). The product (2,5-dimethoxy-2,5-dimethyl-2,5-disila-1,4-dioxane, 79.7 mmol, 64% of theory, purity 97.1% (GC area %)) was obtained as a colorless liquid. According to GC and NMR, it consists of two ax/eq isomers in a ratio of 1.1:1 (these are the cis/trans isomers of 2,5-dimethoxy-2,5-dimethyl-2,5-disila-1,4-dioxane), and contained only 0.6% (GC area %) of (acetoxymethyl)-methyldimethoxysilane and 0.2% (GC area %) of methyl acetate. The bottoms contained catalyst.

Example 6

2,2,5,5-Tetramethoxy-2,5-disila-1,4-dioxacyclohexane and 2,2,5-trimethoxy-5-methyl-2,5-disila-1,4-dioxacyclohexane (catalyst: dioctyltin oxide)

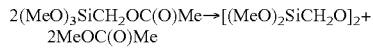

A mixture of 97.1 g of silane (containing 97.4% (GC area %) of (acetoxymethyl)trimethoxysilane, corresponding to 487 mmol, and 2.6% (GC area %) of (acetoxymethyl) dimethoxymethylsilane, corresponding to 14.2 mmol) and 0.9 g of dioctyltin oxide (2.5 mmol) was heated to 120° C. under a nitrogen atmosphere. Within 2 hours, 26.7 g of methyl acetate (360 mmol) were distilled off therefrom using a Widmer column at 1 bar and bottom temperature 80-120° C. Thereafter, under reflux cooling, a dynamic vacuum was applied, which was increased to 95 mbar at bottom temperature 113-124° C. within 3 hours. The methyl acetate formed was condensed in a cold trap at −78° C. (7.9 g, 107 mmol). Thereafter, the reflux cooling was switched off and 10.5 g of distillate were removed at 0.33 mbar, bottom temperature 113-124° C. and top temperature 33-35° C. According to GC and GC-MS, the colorless liquid consisted of 75.0% (GC area %) of 2,2,5,5-tetramethoxy-2,5-disila-1,4-dioxacyclohexane (32.8 mmol, 13% of theory relative to the amount of (acetoxymethyl)trimethoxysilane used) and 22.1% (GC area %) of 2,2,5-trimethoxy-5-methyl-2,5-disila-1,4-dioxacyclohexane (10.3 mmol, 73% of theory based on the amount of (acetoxymethyl)dimethoxymethylsilane used, or 2% of theory based on the amount of (acetoxymethyl)trimethoxysilane used). It contained only 0.35% (GC area %) of (acetoxymethyl)trimethoxysilane and 0.1% (GC area %) of methyl acetate. Thereafter, 38.8 g of further colorless distillate were removed at 0.11-0.16 mbar, bottom temperature 105-120° C. and top temperature 46-84° C. According to GC and GC-MS, it consisted predominantly of oligomers and still contained 35.3% (GC area %) of 2,2,5,5-tetramethoxy-2,5-disila-1,4-dioxacyclohexane (57.0 mmol, 23% of theory based on the amount of (acetoxymethyl)trimethoxysilane used) and 0.2% (GC area %) of 2,2,5-trimethoxy-5-methyl-1,4-dioxa-2,5-disilacyclohexane (0.3 mmol, 2% of theory based on the amount of (acetoxymethyl)dimethoxymethylsilane used, 0.06% of theory based on the amount of (acetoxymethyl)trimethoxysilane used). The bottoms contained catalyst.

Example 7

2,2,5,5-Tetramethyl-2,5-disila-1,4-dioxacyclohexane (catalyst: titanium(IV) n-butoxide)

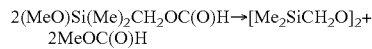

A mixture of 74.1 g of (formoxymethyl)dimethylmethoxysilane (500 mmol) and 1.7 g of titanium(IV) n-butoxide (5 mmol) was heated to 120° C. under a nitrogen atmosphere. Within 2 hours, 19.3 g of methyl formate (321 mmol) were distilled off therefrom at 1 bar and bottom temperature 80-128° C. Thereafter, under reflux cooling, a dynamic vacuum of 360 mbar was applied, which was increased to 70 mbar at bottom temperature 120° C. within 5 hours. The methyl formate formed was condensed in a cold trap at −78° C. (3.3 g, 55 mmol). Thereafter, the reflux cooling was switched off and 18.9 g of distillate were removed at 11 mbar, bottom temperature 113-126° C. and top temperature 42° C. The product (2,2,5,5-tetramethyl-2,5-disila-1,4-dioxacyclohexane, 104 mmol, 42% of theory, purity 97.4% (GC area %)) was obtained as a colorless liquid. It contained 1.4% (GC area %) of (formoxymethyl)dimethylmethoxysilane and 0.1% (GC area %) of methyl formate. The bottoms contained catalyst.

Example 8

2,2,5,5-Tetramethyl-2,5-disila-1,4-dioxacyclohexane (catalyst: dioctyltin oxide; 2-(2-ethoxy-ethoxy)ethyl acetate)

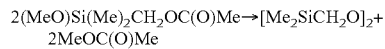

A mixture of 81.1 g of (acetoxymethyl)dimethylmethoxysilane (500 mmol), 1.8 g of dioctyltin oxide (5 mmol) and 0.44 g of 2-(2-ethoxyethoxy)ethyl acetate (2.5 mmol) was heated to 120° C. under a nitrogen atmosphere. Within 2.5 hours, 17.0 g of methyl acetate (229.5 mmol) were distilled off therefrom at 1 bar and bottom temperature 112-120° C. Thereafter, under reflux cooling, a dynamic vacuum of 450 mbar was applied, which was increased to 50 mbar at bottom temperature 109-129° C. within 8 hours. The methyl acetate formed was condensed in a cold trap at −78° C. (6.9 g, 93 mmol). Thereafter, the reflux cooling was switched off and 38.1 g of distillate were removed at 12-15 mbar, bottom temperature 103-120° C. and top temperature 46° C. The product (2,2,5,5-tetramethyl-2,5-disila-1,4-dioxacyclohexane, 213 mmol, 85% of theory, purity 99.4% (GC area %)) was obtained as a colorless liquid. It contained 0.4% (GC area %) of (acetoxymethyl)-dimethylmethoxysilane and 0.2% (GC area %) of methyl acetate. The bottoms contained catalyst.

Example 8 shows, in comparison with example 1, that the addition of an ester shortens the reaction time with the same product quality. Further comparative tests, which were conducted analogously to example 1 and in which no ester addition but ratios of silane to dioctyltin oxide of 200:1 (0.5 mol % of catalyst) to 20:1 (5 mol % of catalyst) were used, did not show any shortening of the reaction time with an increasing relative amount of catalyst.

Example 9

2,2,5,5-Tetramethyl-2,5-disila-1,4-dioxacyclohexane (catalyst: dioctyltin oxide; methanol)

2MeOMe$_2$SiCH$_2$OC(O)Me → [Me$_2$SiCH$_2$O]$_2$ + 2MeOC(O)Me

A mixture of 81.1 g of (acetoxymethyl)dimethylmethoxysilane (500 mmol) and 0.9 g of dioctyltin oxide (2.5 mmol) was heated to 120° C. under a nitrogen atmosphere. Within 2.5 hours, 14.1 g of methyl acetate (190.3 mmol) were distilled off therefrom at 1 bar and bottom temperature 108-122° C. Thereafter, 16 g of methanol (500 mmol) were added and the mixture was heated under reflux cooling for 2 hours (bottom temperature 70-74° C.). Subsequently, the reflux cooling was switched off and 32.1 g of colorless distillate were removed at 1 bar, bottom temperature 74-160° C. and top temperature 50-57° C., which consisted of 61% (GC area %) of methyl acetate (~263 mmol) and 39% (GC area %) of methanol (~388 mmol). Thereafter, 38.2 g of distillate were removed at 10-11 mbar, bottom temperature 105-130° C. and top temperature 41-42° C. The product (2,2,5,5-tetramethyl-2,5-disila-1,4-dioxacyclohexane, 213 mmol, 85% of theory, purity 98.2% (GC area %)) was obtained as a colorless liquid. It contained 0.8% (GC area %) of (hydroxymethyl)dimethylmethoxysilane, 0.1% (GC area %) of (acetoxymethyl)-dimethylmethoxysilane, 0.1% (GC area %) of methanol and less than 0.1% (GC area %) of methyl acetate. The bottoms contained catalyst.

Example 9 shows, in comparison with example 1, that the addition of an alcohol shortens the reaction time with the same product quality.

The invention claimed is:

1. A process for preparing silaoxacycles of the formula I

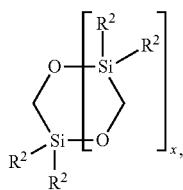

(I)

comprising reacting compounds of the formula II

R$^1$—C(=O)—[O—CH$_2$—Si(R$^2$)$_2$]$_n$—OR$^3$  (II)

to form compounds of the formula (I) in the presence of at least one catalyst comprising a metal of groups 3 to 15 and the lanthanides of the Periodic Table of the Elements according to IUPAC notation, or compound(s) thereof, where x is an integer ≥0,
n is an integer ≥1,
R$^1$ is hydrogen or a hydrocarbyl radical which is unsubstituted or is substituted by one or more Q$^1$ groups and is optionally interrupted by one or more heteroatoms or is an OR$^3$ group,
R$^2$ is hydrogen or a hydrocarbyl radical which is unsubstituted or is substituted by one or more Q$^1$ groups and is optionally interrupted by one or more heteroatoms or is an OR$^4$ group,
R$^3$ is a hydrocarbyl radical which is unsubstituted or is substituted by one or more Q$^1$ groups and is optionally interrupted by one or more heteroatoms,
R$^4$ is a hydrocarbyl radical which is unsubstituted or is substituted by one or more Q$^1$ groups and is optionally interrupted by one or more heteroatoms, or is a CH$_2$Si(R$^5$)$_{3-q}$\{OCH$_2$Si(R$^5$)$_{3-r}$[OCH$_2$Si(R$^5$)$_2$(OR$^3$)]$_r$\}$_q$ group,
q is an integer of 0, 1, 2 or 3,
r is an integer of 0, 1, 2 or 3,
R$^5$ is hydrogen or a hydrocarbyl radical which is unsubstituted or is substituted by one or more Q$^1$ groups and is optionally interrupted by one or more heteroatoms, or an OR$^3$ group, and
Q$^1$ is a monovalent, divalent or trivalent heteroatom-containing radical,
where R$^1$, R$^2$, R$^3$, R$^4$, R$^5$ and Q$^1$ are optionally joined to one another so as to form one or more rings.

2. The process of in claim 1, wherein at least one compound of the formula I is isolated from the reaction mixture.

3. The process of claim 2, in which isolation of a compound of the formula I from the reaction mixture is accomplished by distillation, in which case a compound of the formula I is distilled over as a distillate.

4. The process as claimed in claim 1, in which x has a value of from 1 to 3.

5. The process of claim 1, in which R$^1$ is a hydrogen atom, a C$_1$-C$_{12}$ alkyl radical, a C$_6$-C$_{12}$ aryl radical, a C$_7$-C$_{12}$ alkylaryl radical or a C$_7$-C$_{12}$ arylalkyl radical.

6. The process of claim 1, in which R$^2$ is a C$_1$-C$_{12}$ alkyl radical, a C$_6$-C$_{12}$ aryl radical, a C$_7$-C$_{12}$ alkylaryl radical or a C$_7$-C$_{12}$ arylalkyl radical, a C$_1$-C$_{12}$ alkoxy radical, a C$_2$-C$_{12}$ (alkoxy)alkoxy radical, a C$_6$-C$_{12}$ aryloxy radical, a C$_7$-C$_{12}$ arylalkoxy radical or a C$_7$-C$_{12}$ alkylaryloxy radical.

7. The process of claim 1, in which R$^3$ is a C$_1$-C$_{12}$ alkyl radical, a C$_6$-C$_{12}$ aryl radical, a C$_7$-C$_{12}$ alkylaryl radical, a C$_7$-C$_{12}$ arylalkyl radical or a C$_2$-C$_{12}$ (alkoxy)alkyl radical.

8. The process of claim 1, in which the R$^1$ radical is a hydrogen atom, a methyl group or an ethyl group, the R$^2$ radicals are each independently methyl, methoxy or ethoxy groups, the R$^3$ radical is a methyl or ethyl group, n assumes an integral value from 1 to 3, and x assumes an integral value from 1 to 3.

9. The process of claim 1, in which at least one catalyst is a metal selected from the group consisting of titanium, iron, cobalt, nickel, zinc, aluminum, tin, lead and bismuth, and compounds thereof.

* * * * *